United States Patent [19]

Seman

[11] Patent Number: 5,320,968
[45] Date of Patent: Jun. 14, 1994

[54] METHOD FOR DETECTING LIPOPROTEIN (A) AND ASSOCIATED CHOLESTEROL

[76] Inventor: Leo J. Seman, 37 Ashwood Ave., Methuen, Mass. 03079

[21] Appl. No.: 21,189

[22] Filed: Feb. 23, 1993

Related U.S. Application Data

[63] Continuation-in-part of Ser. No. 704,457, May 23, 1991, abandoned.

[51] Int. Cl.$^5$ .................. G01N 33/53; G01N 33/549; G01N 33/92
[52] U.S. Cl. ..................... 436/71; 436/518; 436/535; 435/7.1; 435/11; 435/19; 435/28
[58] Field of Search .............. 436/71, 518, 532, 535; 435/7.1, 11, 19, 28

[56] References Cited

U.S. PATENT DOCUMENTS

| | | | |
|---|---|---|---|
| 4,126,416 | 11/1978 | Sears | 23/230 B |
| 4,366,244 | 12/1982 | Pascal | 435/11 |
| 4,877,746 | 10/1989 | Jansson et al. | 436/518 |

*Primary Examiner*—James C. Housel
*Assistant Examiner*—David Redding
*Attorney, Agent, or Firm*—Peter J. Dehlinger

[57] ABSTRACT

A method for assaying lipoprotein (a) in a liquid sample containing other lipoproteins, and a assay device for use in the method are disclosed. In the method, the liquid is contacted with a solid-support reagent containing lectin attached to a solid support, under conditions effective to bind of lipoprotein (a) to the support-bound lectin. After removing unbound lipoproteins, the amount of lipoprotein (a) bound to the support is assayed. In one embodiment, the method and assay device are designed for assaying cholesterol associated with lipoprotein (a).

12 Claims, 1 Drawing Sheet

■ VDL
● LDL
○ VLDL

METHOD FOR DETECTING LIPOPROTEIN (A) AND ASSOCIATED CHOLESTEROL

This application is a continuation-in-part of application Ser. No. 07/704,457, filed May 23, 1991 now abandoned.

1. FIELD OF THE INVENTION

The present invention relates to diagnostic methods, and particularly, to diagnostic methods for measuring serum levels of lipoprotein (a).

2. BACKGROUND OF THE INVENTION

Cholesterol is transported in the blood by lipid-containing particles known as lipoproteins. The most important of these lipoproteins are high density lipoprotein (HDL), low density lipoprotein (LDL), very low density lipoprotein (VLDL), and lipoprotein (a), (Lp(a)). Of these components, HDL cholesterol can be measured directly by precipitating all apoB-containing lipoproteins (VLDL, LDL and Lp(a)). VLDL is the only fasting lipoprotein with triglyceride as the major lipid component. There are usually four grams of triglycerides for every gram of cholesterol in VLDL. LDL has traditionally been estimated by subtraction of HDL and VLDL cholesterol from total cholesterol.

Recently it has been demonstrated that Lp(a) is an important cholesterol-containing blood constituent. Several recent case-control studies have shown that plasma Lp(a) is elevated in subjects with coronary artery disease and advanced atherosclerosis. Lp(a) plasma levels appear to be inherited and do not fluctuate with diet. However, Lp(a) plasma levels can be reduced with niacin and neomycin. Since treatment is possible, screening the general public as part of a total lipid profile determination is a practical approach to identifying and reducing this risk factor.

Lp(a) has never been measured as a cholesterolcontaining blood component. In the past, only protein components of the Lp(a) molecule were measured. Today, most researchers have adopted the practice of estimating the entire mass of Lp(a) by estimating its most unique cholesterol apolipoprotein, namely apo(a). Not only does Lp(a) contain cholesterol (approximately 25% of total mass), it also contains apoB$_{100}$, apo(a) and small amounts of triglyceride and phospholipid. Apo(a) accounts for only 8%-12% of the total mass of Lp(a).

Heretofore, several diagnostic kits based on ELISA technology have been proposed for measuring Lp(a). ELISA tests require a monoclonal antibody to detect a unique feature of Lp(a), of which there are few. The only component of Lp(a) that is unique to Lp(a) are small regions within the apo(a) molecule. The apo(a) molecule in total is not very unique since it is composed of regions that have 78-95% homology with another plasma protein, namely plasminogen. The largest portion of the apo(a) molecule is composed of repeating sequences of approximately 20,000 daltons that have 78-84% homology with the plasminogen region called kringle IV. The most unique feature of apo(a) is its high carbohydrate content. However, carbohydrate is not very antigenic in nature and would not be expected to contribute much to the development of unique monoclonal antibodies. These features make the production of monoclonal antibodies which react specifically to apo(a), and not to plasminogen, very difficult.

It would therefore be useful to have a simple, reliable test for measuring Lp(a). Current methods for determining Lp(a)-associated cholesterol indirectly by first determining apo(a) concentrations have a margin of error of + or −5%. This is due, in part, to the fact that apo(a) exists in a number of isoforms which can vary in mass by up to 50%. The method disclosed herein is a direct Lp(a) cholesterol determination and has a margin or error of + or −1%.

3. SUMMARY OF THE INVENTION

The invention includes, in one aspect, a method for assaying Lp(a) in a liquid sample containing one or more other serum lipoproteins. The method involves first contacting the liquid sample with a solid-support reagent composed of lectin attached to a solid support, under conditions effective to bind of Lp(a) to the support-bound lectin. After removing lipoproteins in the sample which are not bound to the support, the Lp(a) remaining is assayed.

In one embodiment, the lectin binds specifically to Lp(a) N-acetyl-D-glucosamine or N-acetylneuraminic acid monosaccharide units, and is preferably a wheat germ agglutinin, lima bean agglutinin, phytohemagglutinin or horseshoe crab lectin. The binding reaction is preferably carried out at a pH between about 6.9 to 7.5.

One preferred assay is for determination of cholesterol associated with Lp(a), as a method for measuring Lp(a). In this embodiment, the supportbound Lp(a) may be treated with a surfactant effective to disrupt Lp(a), and cholesterol esterase, and the released, free cholesterol may be assayed by conventional reaction with cholesterol oxidase and a peroxidase/dye system.

In a related aspect, the invention includes a method for isolating Lp(a) essentially free from other proteins, from a liquid sample, where the Lp(a) bound to the solid support is isolated from other lipoproteins, then released by eluting Lp(a) from the washed support.

Also disclosed is an assay device for use in assaying Lp(a) in a blood-fluid sample. The device includes a solid-support matrix having a binding region of attached lectin molecules, and matrix structure on which a sample is introduced into the matrix, for movement of sample components through the binding region. The device further includes a reagent pad containing reagents for releasing cholesterol from Lp(a) bound to the support, and for assaying free cholesterol.

These and other objects and features of the invention will become more fully apparent when the following detailed description of the invention is read in conjunction with the accompanying drawings.

DETAILED DESCRIPTION OF THE INVENTION

A. Solid Support Reagent

Figure 1:
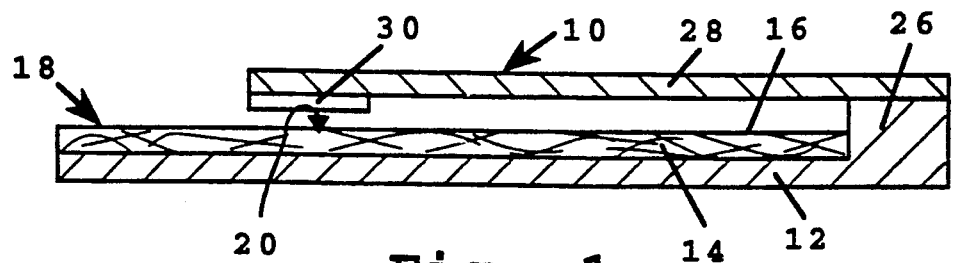
FIG. 1 is a side sectional view of an assay device designed for assaying Lp(a)-associated cholesterol, in accordance with the invention.

The method of the invention employs a solid support reagent for capturing Lp(a) selectively in a fluid sample containing other lipoproteins, such as LDL, VLDL, and HDL. The solid-support reagent includes a solid support and attached thereto, preferably by covalent chemical attachment, a lectin effective to bind selectively to Lp(a). Preferred lectins for use in the methods described herein are selected from the group of lectins which specifically bind to either GlcNAc or NANA, which are prominent residues in Lp(a). This group of lectins includes, for example, wheat germ agglutinin, phytohemagglutinin, lima bean agglutinins and horseshoe crab lectins. All of these lectins are available from commercial suppliers.

Attachment of lectins to a solid support can be carried out according to known derivatization methods. Activatable beads (e.g. agarose, acrylamide or glass) are preferred as the solid substrate. A variety of known methods are available for use in attaching a protein (e.g. a lectin) to a bead substrate. The most common method for the covalent attachment of a protein to a bead is to activate the bead using any of a number of chemical agents and then bind the protein to the beads. This approach offers several advantages. Generally, the beads can be activated under harsh conditions without any decrease in coupling efficiency thereby allowing the use of a range of activating protocols.

Preparing activated beads is relatively inexpensive, and many of the coupling methods yield a linkage that is stable to a wide range of denaturing conditions. Another advantage is that there are a number of activated beads available commercially. An alternative is to activate lectin itself; however, the specificity of the lectin for Lp(a) may be adversely affected by such a treatment. Table 1 presents a partial list of activatable bead types, functional groups and activating compounds. Of the methods listed in Table 1, cyanogen bromide activation is the most commonly used. Cyanogen bromide offers a high coupling capacity, and an extensive body of literature has developed on the technique.

TABLE 1

| Bead | Functional Group | Activating Compound |
| --- | --- | --- |
| Agarose Beads | —OH | Cyanogen bromide Carbonyldiimidazole |
| Cross-linked Agarose Beads | —OH | Cyanogen bromide Carbonyldiimidazole Tosyl chloride |
| Polyacrylamide | —NH$_2$ | Glutaraldehyde |
| Copolymers of Polyacrylamide and Agarose beads | —OH —NH$_2$ | Cyanogen bromide Carbonyldiimidazole Glutaraldehyde |
| Polyacrylic Beads | —OH | Cyanogen bromide Carbonyldiimidazole Tosyl chloride |

Another method for the attachment of a lectin to a column packing material is by coupling the lectin with a bifunctional reagent, one group binding to an appropriate group in the lectin and the other remaining free to bind to the functional group on the solid substrate. Reagents that are commonly used for indirect coupling are the water soluble carbodiimides such as: (1) 1-ethyl-3-(3-dimethylaminopropyl)-carbodiimide HCl (EDAC or EDCI) or 1-cyclohexyl-3-(2-morpholinoethyl)-carbodiimidemetho-p-toluene-sulfonate (CMIC or CMCI); (2) the condensing agents for peptide synthesis such as N-ethoxycarbonyl-2-ethoxy-1,2-dihydroquinoline (EEDQ); (3) glutaraldehyde or (4) periodate.

After the proteins are activated, they are bound to the column packing beads. Proteins activated by carbodiimides and condensing reagents will bind to carboxylic acid, while the glutaraldehyde and periodate-activated antibodies will bind to amines. In addition to the coupling methods specifically recited herein, a variety of other methods are well known to those skilled in the art.

In the case of solid bead particles, the beads can be formed as an aqueous buffer suspensions and transferred to an column suitable for affinity chromatography, e.g., having a semi-permeable barrier at the bottom of the column. As the colloids settle from the suspension a bed is formed. Interstitial space exists within the column bed, either between the beads or through pores in the beads, which allows the flow of protein through the column bed with the buffer. Thus, the surface area to which the affinity reagent is attached is extraordinarily high for any given column volume (compared, for example, to attaching an affinity reagent to a micro-welled plate or a membrane). Not only is the surface area extremely high, but a column can be adapted for continuous sample flow thereby simplifying purification from a relatively large volume (relative to the column volume).

Lectin bound to activated beads can also be used to bind Lp(a) in a constantly mixing slurry of lectin-beads with soluble Lp(a), as opposed to their use in an affinity column. However, following incubation in the slurry for an appropriate period, the beads must be collected and washed prior to elution of bound Lp(a). The column is preferred as it does not require such manipulation.

A wide variety of solid substrates are useful 15 as an alternative to a bead-type solid support. Examples include formed plastic substrates (e.g. micro-well plates, membrane sheets, etc.), many of which are activatable by methods analogous to those described above. Methods for attaching proteins to such substrates are well known in the art. In one embodiment, for use in a dry-pad assay for assaying serum cholesterol associated with Lp(a) (described below), the solid support substrate is a glass-fiber filter matrix. Methods for activating glass fibers (or modifying the glass fiber surface to contain reactive groups), and for covalently attaching proteins to the modified fibers are well known.

B. Binding Lp(a) to the Support

A liquid sample to be tested for the presence of Lp(a) or Lp(a)-associated cholesterol is contacted with the solid support reagent and incubated under conditions appropriate for the binding of Lp(a) to the lectin. The liquid sample and the substrate are separated from one another and the support may be washed to remove non-specifically bound components. Lp(a) is then released from the lectin, or disrupted to release individual components, such as cholesterol, as described below.

A wide range of conditions are appropriate for selective binding of Lp(a) to the support-bound lectin. For example, the optimal pH range for the use of the lectin wheat germ agglutinin is about 6.9 to 7.5. As indicated in the Exemplification which follows, surprisingly effective purification from other lipoproteins was achieved at a pH of about 7.4. The ionic strength of the liquid solution is preferably within physiological limits (i.e. less than about 400 mM). There is a wide range of temperatures at which Lp(a) binds efficiently to wheat germ agglutinin. For example, the methods described herein have been successfully conducted at temperatures ranging from 4°–37° C.

After the step in which Lp(a) is bound to the solid-support reagent, the support reagent may be washed with a wash solution to remove non-specifically bound material. The properties of the wash solution (e.g. pH, ionic strength, etc.) are selected so as not to disrupt the specific binding interaction between the lectin and Lp(a).

Following the wash step, the Lp(a) can be released from the support reagent by conventional methods. For example, the bound Lp(a) can be released by contacting the solid substrate with a solution having properties (e.g. pH or ionic strength) which serve to disrupt the specific interaction between the Lp(a) and the lectin. Alternatively, the bound Lp(a) can be released by contacting the solid substrate with a solution containing a molecule which competes with Lp(a) for lectin binding. An example of such a molecule, for use with the preferred lectins referred to above, is N-acetyl-D-glucosamine or N-acetylNeuroaminic acid. A concentrated solution of such a competitor molecule, which contacted with Lp(a) bound to a preferred lectin, results in the release of Lp(a) from the solid substrate.

The method for isolating Lp(a) essentially free from other lipoproteins can be adapted to achieve a variety of goals. For example, the amount of lectin-bound Lp(a) which is released from the solid substrate can be used to calculate the concentration of the Lp(a) in the liquid sample. Many epidemiologic studies from Europe and North America have found that when plasma levels of Lp(a) exceed 0.20 g/L, there is a significantly higher risk of coronary and cerebrovascular atherosclerosis (see e.g. Hegels, *Can. J. Cardiol.* 5:263–265).

Released Lp(a) can be assayed, for example, by one of a variety of solid-phase assay formats employing a reporter-labeled anti-Lp(a) or lectin reagent for specific binding to Lp(a). Alternatively, the Lp(a) may be assayed directly, without eluting from the solid-support reagent. In one assay format, the bound Lp(a) is reacted with a reporterlabeled anti-Lp(a) antibody, such as peroxidaselabeled anti-Lp(a), and the solid support is then examined for bound reporter.

In another general embodiment, Lp(a) captured on the solid-support reagent is assayed indirectly, by measuring the amount of cholesterol associated with bound or released Lp(a). This can be accomplished by conventional methods for determining cholesterol concentrations which are well known to those skilled in the art. Such methods include, for example, the cholesterol-esterase and cholesterol oxidase enzymatic assays, as described below.

C. Lp(a) Assay Device and Method

In one embodiment of the invention, the method is used to assay serum Lp(a), by assaying the amount of cholesterol associated with support-bound Lp(a). An assay device designed for carrying out the method is illustrated at 10 in FIG. 1. The device includes a base 12 on which is supported a fiber matrix 14 in the form of a rectangular strip 16. The matrix is a wettable matrix, such that liquid applied to a surface of the matrix is drawn into and through the matrix by capillarity. One preferred matrix is a glass fiber filter, such as a GF/D or PD008 filter supplied by Whatman, having a packing density of about 0.16 g/cm³. The matrix is cut to side dimensions of about 5×40 mm, and a thickness of about 1 mm.

The left end region of the matrix defines a sample-application region 18, at which sample is introduced into the matrix. From here the sample is drawn by capillarity to the right in the figure through a binding region 20, and toward the right end region of the matrix. A magnified portion of the binding region is shown in simplified view in FIG. 2. In this region, the fibers which make up the region, such as fibers 22, are derivatized with lectin molecules (L), such as molecule 24, and thus form the solid-support reagent in the device.

The glass fibers in the binding region of the matrix are derivatized with lectin according to above-described methods. The derivatization region can be confined to one region of the matrix strip, for example, by tightly clamping the strip on either side of the region during derivatization, to prevent flow of the derivatization reaction fluid beyond the desired binding region.

Completing the description of the assay device shown in FIG. 1, base 12 terminates at its right end in the figure at a block 26 on which is supported a cantilever 28 which carries at its lower right end region, a reagent pad 30. The pad is a fluid-absorbent pad, such as a glass matrix pad in which are embedded (a) reagents for releasing free cholesterol from Lp(a), and (b) reagents for assaying free (non-esterified) cholesterol.

In a preferred embodiment, the releasing reagents include a surfactant, preferably a conventional non-ionic surfactant such as a Tween ™ or Triton-X ™ type surfactant, which is effective to disrupt Lp(a), with the release of free and esterified forms of cholesterol in the Lp(a) particle.

Also in a preferred embodiment, the assaying reagent includes cholesterol oxidase, which is effective to generate $H_2O_2$ in the presence of free cholesterol, a peroxidase enzyme, and a peroxidasesubstrate dye which undergoes a pronounced color change when it is oxidized by $H_2O_2$ in the presence of the peroxidase enzyme, Such peroxidase/dye systems for quantitating $H_2O_2$, such as generated by a substrate-dependent oxidase enzyme, are well known in the art.

The releasing and assaying reagent components may be embedded in the pad by infusing a solution of the components into the pad, and drying the infused pad, conventionally.

In operation, a blood-fluid sample, such as a serum sample, is applied to region 18 of the matrix, from which the fluid is drawn into and through the matrix, toward the right in the figure. The application region, and the underlying portion of the matrix thus serves as means for introducing a sample into the matrix.

Figure 2:
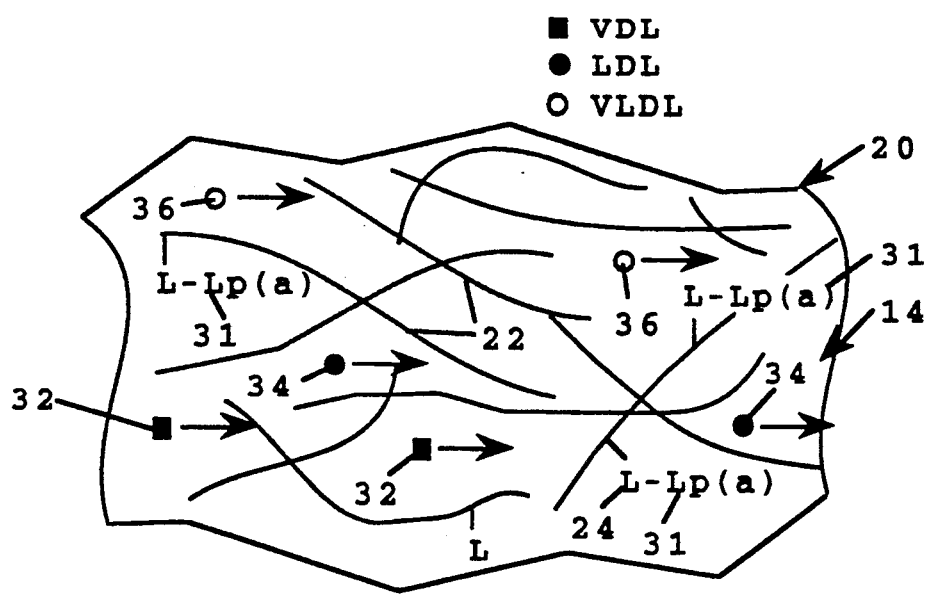
FIG. 2 illustrates the selective capture of Lp(a) particles in a serum sample in a binding region of the assay device.
Figure 3:
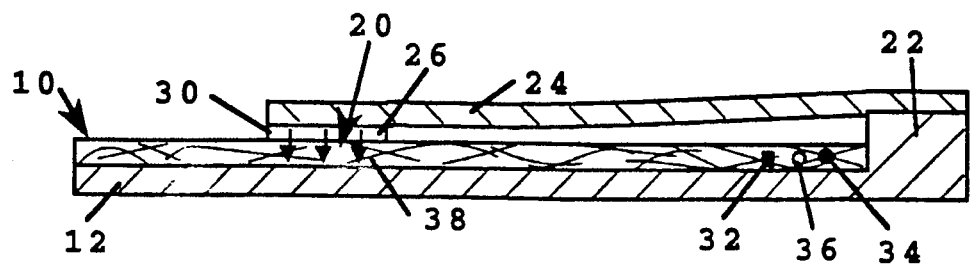
FIG. 3 shows the operation of the assay device to bring cholesterol-release and cholesterolassay reagents into contact with Lp(a) immobilized in the binding region of the matrix device.

As the sample passes through the binding region of the matrix, Lp(a) particles in the sample, such as indicated at 31, bind specifically to lectin (L) molecules attached to the matrix fibers, as indicated in FIG. 2. At the same time, other lipoprotein components, such as LDL particles 32 (solid squares), VLDL particles 34 (solid circles), and HDL particles 36 (open circles) move through the binding region toward the right end region of the strip, as illustrated in FIG. 3. The movement of fluid through the matrix is thus effective to bind Lp(a) particles selectively to the solid-support matrix fibers in the binding region of the matrix, and separate the Lp(a) from other lipoproteins contained in the sample.

After the binding and separation step, cantilever 24 is manipulated to bring pad 30 on the cantilever into contact with the binding region (solid support reagent) of the matrix, as illustrated in FIG. 3. This allows fluid in the matrix to wet the pad, and form a solution of reagent components in the pad, which can now flow into the adjacent binding region, as indicate by arrows 38, and mix the reagent in the pad with the bound Lp(a). The cantilever thus provides means for bringing the reagent pad into contact with the matrix binding region.

The release components in the pad are effective, when introduced into the binding region, to release cholesterol from bound Lp(a) particles, and convert the released cholesterol to free cholesterol. The free cholesterol in turn, acts as a substrate for the assay reagent components, such as cholesterol oxidase. Free cholesterol can then be quantitated by a standard colorimetric reaction, such as one involving the components discussed above.

Exemplification

Wheat germ agglutinin was immobilized on CNBr-activated Sepharose TM 4B (Pharmacia) according to the manu-facturer's instructions. The immobilized wheat germ agglutinin was washed with a standard sodium phosphate buffered saline solution, pH 7.4. Human plasma having Lp(a) concentrations (i.e. total Lp(a) mass) ranging from 2 mg/dL to 80 mg/dL, with triglyceride concentrations ranging from 37 mg/dL to 1850 mg/dL, were poured over immobilized WGA-4% agarose (which contains about 6.5-7.6 mg WGA per ml). The columns were washed with 10 volumes PBS (pH 7.4) containing 0.3 mM $Na_2$ EDTA to prevent fibrin formation in the plasma. The columns were then eluted with 2-3 volumes of PBS containing GlcNAc (100 mM).

Lp(a) and cholesterol were measured in all fractions. Lp(a) levels were determined using the Lp(a) Macra TM kit provided by Terumo diagnostics (Elkin, Md.). Cholesterol levels were determined on an Abbott autoanalyzer. The following results were obtained. All of the Lp(a) in the sample were detected in the GlcNAc eluted volume. No Lp(a) was detected in the PBS washes. The amount of Lp(a) in the GlcNAc eluates equalled that found in the initial plasmas (as determined by Lp(a) Macra). The Abbott autoanalyzer gave the same results in the presence of 100 mM GlcNAc in PBS, as in PBS alone. The cholesterol (in mg/dL) determined in the GlcNAc eluate was consistently 25-26% of the total mass of Lp(a), as estimated by Lp(a) Macra. The GlcNAc eluate contained only a prebeta-1 particle that comigrated with pure Lp(a) and migrated slightly slower than the VLDL in the whole plasma on agarose gel electrophoresis. An immunoblot of this gel demonstrated reactivity of this prebeta 1 band with antibodies to apoB and a monoclonal antibody to apo(a) that does not cross-react with plasminogen (supplied by Terumo).

These results essentially confirm identity between the GlcNAc eluted lipoprotein and Lp(a). In a subject with 35 mg/dL Lp(a) mass in plasma, Lp(a) composes only 35% of the total mass of proteins that bind to the WGA. However, Lp(a) is the only plasma lipoprotein which is retained on the WGA-agarose column.

Although the invention has been described with respect to particular embodiments and methods, those skilled in the art will know, or be able to ascertain using no more than routine experimentation, many equivalents to the specific embodiments of the invention described herein. These and all other equivalents are intended to be encompassed by the following claims.

It is claimed:

1. A method for assaying lipoprotein (a) in a liquid sample containing one or more other serum lipoproteins and having a pH of about 6.9-7.5, comprising the steps of:
   a) contacting the liquid sample with a solid-support reagent containing lectin attached to a solid support, under conditions effective to bind lipoprotein (a) to the support-bound lectin;
   b) removing lipoproteins in the sample which are not bound to the support, and
   c) assaying the lipoprotein (a) remaining after said removing.

2. The method of claim 1, wherein the lectin binds specifically to lipoprotein (a) monosaccharide units selected from the group consisting of N-acetyl-D-glucosamine and N-acetylneuroaminic acid.

3. A method of claim 2, wherein the lectin is selected from the group consisting of wheat germ agglutinin, lima bean agglutinins, phytohemagglutinin and horseshoe crab lectins.

4. The method of claim 1, wherein said removing includes washing the solid support to remove lipoproteins which are not specifically bound to the lectin on the solid support.

5. The method of claim 1, wherein said assaying includes removing lipoprotein (a) bound to the solid support, and assaying the released lipoprotein (a) .

6. The method of claim 1, wherein said assaying includes releasing cholesterol from the lipoprotein (a), and assaying released cholesterol.

7. The method of claim 6, wherein said assaying includes treating the lipoprotein (a) with cholesterol esterase and a surfactant, to release cholesterol from the lipoprotein (a), reacting the released cholesterol with cholesterol oxidase, to produce $H_2O_2$, and assaying for produced $H_2O_2$ using a peroxidase enzyme.

8. A method of assaying for cholesterol content of lipoprotein (a) in a blood-fluid sample having a pH of about 6.9-7.5, comprising the steps of
   passing the blood-fluid sample through a solid-support matrix having a binding region of attached lectin molecules, thereby to bind lipoprotein (a) particles in the sample selectively in the binding region, by lipoprotein (a) binding to the support-bound lectin,
   removing non-bound cholesterol components from the binding region of the matrix, and
   assaying the amount of cholesterol in the lipoprotein (a) bound to the solid support.

9. The method of claim 8, wherein said removing includes passing washing liquid through said matrix region, and said assaying includes releasing cholesterol from the solid-support, and assaying released cholesterol.

10. The method of claim 9, wherein said assaying includes treating the bound lipoprotein (a) with cholesterol esterase and a lipid surfactant, to release cholesterol from the lipoprotein (a), reacting the released cholesterol with cholesterol oxidase, to produce $H_2O_2$, and assaying for produced $H_2O_2$ using a peroxidase enzyme.

11. A method for isolating lipoprotein (a), essentially free from other proteins, from a liquid sample having a pH of about 6.9-7.5 comprising the steps of:
   a) providing a liquid sample containing lipoprotein (a);
   b) contacting the liquid sample with a solid-support reagent containing lectin attached to a solid support, under conditions effective to bind of lipoprotein (a) to the support-bound lectin;

c) washing the affinity column to remove nonspecifically bound material; and d) eluting the lectin-bound lipoprotein (a).

12. The method of claim 11, wherein the liquid sample is contacted with a wheat germ agglutinin in an affinity column under conditions appropriate for the binding of the lipoprotein (a) to the wheat germ agglutinin.

* * * * *